United States Patent [19]
Strandberg et al.

[11] Patent Number: 5,476,496
[45] Date of Patent: Dec. 19, 1995

[54] IMPLANTABLE MEDICAL ELECTRODE SYSTEM HAVING AN INDIFFERENT ELECTRODE FORMED AS A PART OF THE ELECTRODE INSULATOR SLEEVE

[75] Inventors: Hans Strandberg, Sundbyberg; Jakub Hirschberg, Taeby, both of Sweden

[73] Assignee: Pacesetter AB, Solna, Sweden

[21] Appl. No.: 241,397

[22] Filed: May 11, 1994

[30] Foreign Application Priority Data

Jun. 1, 1993 [SE] Sweden .................... 9310857

[51] Int. Cl.⁶ .................... A61N 1/05
[52] U.S. Cl. .................... 607/122
[58] Field of Search .................... 607/122, 123, 607/125, 127; 128/642

[56] References Cited

U.S. PATENT DOCUMENTS

| | | |
|---|---|---|
| 3,915,174 | 10/1975 | Preston . |
| 4,387,717 | 6/1983 | Brownlee et al. . |
| 5,016,646 | 5/1991 | Gotthardt et al. . |
| 5,190,052 | 3/1993 | Schroeppel .................... 607/123 |
| 5,330,520 | 7/1994 | Maddison et al. .................... 607/122 |

FOREIGN PATENT DOCUMENTS

| | | | |
|---|---|---|---|
| 0373953 | 6/1990 | European Pat. Off. . | |
| 0396835 | 11/1990 | European Pat. Off. . | |
| 0269095 | 6/1989 | German Dem. Rep. .................... | 607/122 |
| 2822829 | 11/1979 | Germany .................... | 607/122 |

*Primary Examiner*—George Manuel
*Assistant Examiner*—Jeffrey R. Jastrzab
*Attorney, Agent, or Firm*—Hill, Steadman & Simpson

[57] ABSTRACT

An implantable electrode system includes a connector for connecting a proximal end of the electrode to an implantable medical apparatus, such as for stimulating living tissue, and a distal end at which a tip electrode is located. The proximal end and the distal end are connected by a conductor which electrically connects the medical apparatus to the electrode tip, and which is surrounded by a flexible insulating sleeve. In order to provide an indifferent electrode having a large surface area relative to the size of the tip electrode, the insulating sleeve is provided with a section formed by an electrically conductive, flexible material, which serves as the indifferent electrode. The flexibility of the electrode system is retained, while providing an indifferent electrode of optional size.

6 Claims, 1 Drawing Sheet

IMPLANTABLE MEDICAL ELECTRODE SYSTEM HAVING AN INDIFFERENT ELECTRODE FORMED AS A PART OF THE ELECTRODE INSULATOR SLEEVE

BACKGROUND OF THE INVENTION

1. Field of the Invention

The present invention is directed to an implantable electrode system, such as a medical electrode system for stimulating living tissue as part of an implantable stimulation system.

2. Description of the Prior Art

Electrodes are known which are used in conjunction with implantable medical devices, such as devices for electrically stimulating tissue, such electrodes having a proximal end connectable to the medical device, and a distal end at which a tip electrode is located to deliver electrical stimulation pulses to surrounding tissue. The tip electrode is electrically connected to the medical device by means of a conductor which extends inside a flexible insulating sleeve from the proximal end to the distal end of the electrode. Such a device is also provided with an indifferent electrode, having a large electrode surface relative to the size of the tip electrode, and are typically provided with a second conductor, electrically insulated from the first conductor, connected to the indifferent electrode and to the medical apparatus. Electrical stimulation pulses are emitted by the medical apparatus to the tissue across the tip electrode and the indifferent electrode, and electrical signals arising in the living tissue can be sensed between the tip electrode and the indifferent electrode, and supplied to the medical apparatus for analysis.

A cardiac electrode system is disclosed in U.S. Pat. No. 4,387,717 for stimulating a cardiac heart and sensing cardiac activity. The system includes a first conductor which extends through an insulating sleeve to a tip electrode, which is placed in the heart. A ring electrode is located at a defined distance on the lead from the tip electrode. The ring electrode is connected to a second electrical conductor. The first conductor and the second conductor are connected to a pacemaker. The ring electrode serves as the indifferent electrode, and can be disposed along the lead at a distance from the tip electrode so that the indifferent electrode can be positioned either inside or outside the heart.

Particularly for sensing cardiac activity, it is important that no signals be detected by the indifferent electrode, because such signals could interfere with the interpretation of signals detected by the tip electrode. The indifferent electrode also should have a large surface, in order to reduce the current density in the region surrounding the indifferent electrode, so as to prevent needless or unwanted stimulation of body tissue around the indifferent electrode when the medical apparatus emits a stimulation pulse across the tip electrode and the indifferent electrode. The ring electrode in the known system described in U.S. Pat. No. 4,387,717 cannot be provided with such a large electrode surface, because it is stiff and therefore cannot be permitted to have a large size, because this would make the entire electrode system stiff and impossible to implant. Moreover, even if successfully implanted, a lead having a large area, rigid electrode, such as a ring electrode, may cause damage to the vascular system after implantation.

The indifferent electrode can be provided with a large surface by making the pacemaker enclosure (can) serve as the indifferent electrode. This is a known approach for pacemakers, as described in the aforementioned patent. As a result, however, the indifferent electrode may detect muscle signals from nearby muscle tissue, which would constitute noise interfering with the interpretation of cardiac signals.

Alternatively, a separate, large-area electrode could be applied outside of the heart, apart from the electrode system inside the heart, as also described in the aforementioned patent. This type of indifferent electrode, however, causes complications in implantation, and may also be difficult to affix at a suitable site without resulting in the detection of muscle signals by such an electrode.

An electrode system as disclosed in U.S. Pat. No. 3,915,174 which, in addition to a tip electrode and a ring electrode, is provided with a large-surface indifferent electrode along the length of an electrode catheter. The indifferent electrode is placed on the electrode catheter so that it lies outside of the heart after the electrode system has been implanted. This patent states that the indifferent electrode can be permitted to extend into the heart in an embodiment wherein the indifferent electrode has a size which, in principle, is coextensive with the entire electrode catheter. The indifferent electrode is formed by a cylindrical ring made of a conductive material.

SUMMARY OF THE INVENTION

It is an object of the present invention to provide an implantable electrode system which includes an indifferent electrode, which is easy to manufacture and to implant, and which minimizes the risk of damage to the vascular system after implantation.

The above object is achieved in accordance with the principles of the present invention in an implantable electrode system wherein the insulator sleeve of the electrode lead has a section, disposed between the distal and proximal ends of the lead, which is electrically conductive, but which consists of pliant material. The conductive section thus can serve as the indifferent electrode, but does not affect the flexibility of the overall lead. Utilization of a section of optional length of the insulator sleeve for the indifferent electrode, and making that section electrically conductive, results in an electrode system which solves the aforementioned problems in the art. The indifferent electrode can be provided with a large electrode surface, and can be located at a position along the lead which minimizes the risk of any interference signals being detected. Because the sleeve section itself is made conductive, fabrication of the electrode system is facilitated. The section of the sleeve forming the indifferent electrode is flexible, so that implantation of the electrode system is not impeded, and the vascular system is subjected to minimum trauma after implantation. Additionally, the diameter of the electrode system between the indifferent electrode and the remainder of the sleeve does not change, so that sharp edges, which could damage tissue, are completely avoided.

Preferably, the distal end of the electrode system is devised so as to be introducible into a heart, and the indifferent electrode has a size enabling at least a part of the indifferent electrode to lie outside of the heart, after the distal end has been introduced into the heart and affixed at a desired location.

Because a part of the indifferent electrode is outside of the heart, the indifferent electrode has an area which is larger than the area of the aforementioned ring electrodes known in the art, and therefore the indifferent electrode according to the invention does not detect any signals from the heart itself. Moreover, the indifferent electrode of the invention does not detect any muscle signals, because it is located within the vascular system. This enables signals detected by the tip electrode to be easily interpreted.

In a further embodiment of the invention, the indifferent electrode is formed by a conductive coating extending along a defined section of the insulator sleeve, the conductive coating being electrically connected to the second conductor in the lead.

In this embodiment, the sleeve remains insulating along its entire interior length, but is conductive along a portion of its exterior, in the aforementioned section forming the indifferent electrode. This reduces the risk of any short-circuit developing between the first conductor and the indifferent electrode.

Preferably, the indifferent electrode in the electrode system of the invention is made of a conductive polymer. The conductive polymer will have the same flexible properties as the sleeve, and will therefore not restrict the flexibility and compliance of the electrode system.

In another embodiment, the indifferent electrode is formed by doping a defined section of the insulator sleeve with a conductive material.

When the sleeve is doped with a conductive material, preferably a biocompatible material or a metallic compound such as titanium nitride or platinum, or some other biocompatible conductor such as carbon, the flexing properties of the electrode system are retained, while electrical conductivity is achieved for the defined section of the sleeve.

In another embodiment, a second insulating sleeve is disposed inside of the first insulating sleeve, and the second conductor is helically coiled in a space between the first and second insulating sleeves, with the first conductor being helically coiled inside the second sleeve.

This results in an electrode system wherein the first conductor, which connected to the tip electrode, is well-protected and well-insulated from the second conductor and ambient body fluids.

DESCRIPTION OF THE PREFERRED EMBODIMENTS

Figure 1:
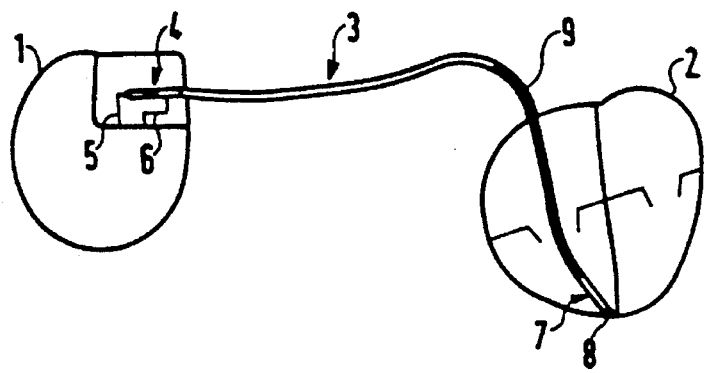
FIG. 1 is a schematic illustration showing an electrode system constructed in accordance with the principles of the present invention connecting a pacemaker and a heart.

FIG. 1 shows a pacemaker 1 connected to a heart 2 via an electrode system 3. The electrode system 3 is connected to the pacemaker 1 at a proximal end 4, the electrode system 3 containing a first conductor 5 and a second conductor 6 which are connected to electronics (not shown) in the pacemaker 1. The electrode system 3 is further connected to the heart 2 at a distal end 7. A tip electrode 8, which is connected to the first conductor 5 and is in contact with heart tissue, is disposed at the distal end 7. The electrode system 3 also has an indifferent electrode 9, which is insulated from the tip electrode 8, and which is designated in FIG. 1 by the darkened section of the electrode system 3. The indifferent electrode 9 is connected to the second conductor 6. The pacemaker 1, via the first conductor 5 and the second conductor 6, emits and receives electrical signals to and from the heart 2. When electrical signals are sensed in the heart 2, the tip electrode 8 detects the signals, and the indifferent electrode 9 remains passive, so that the signals which are obtained are easily interpreted by circuitry in the pacemaker 1. In principle, the indifferent electrode 9 may extend along any desired length of the electrode system 3. It is important, however, that at least a part of the indifferent electrode 9 be located outside of the heart 2, so as to prevent cardiac signals from being detected by the indifferent electrode 9, since this would interfere with interpretation of the sensed signals.

Figure 2:
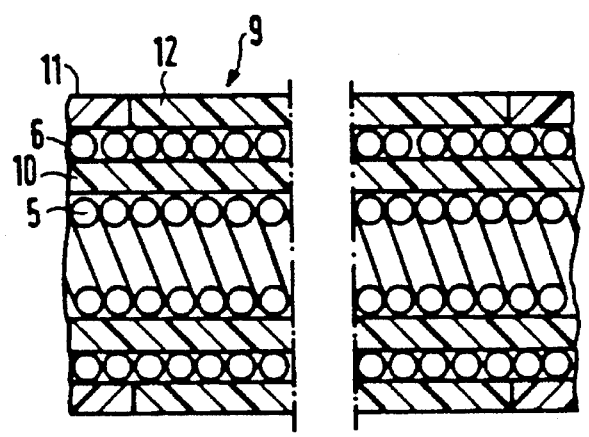
FIG. 2 is an enlarged sectional view of a first embodiment of an indifferent electrode in an electrode system constructed in accordance with the principles of the present invention.

A first embodiment for the indifferent electrode 9 is shown in FIG. 2. Only a part of the electrode system 3 is shown therein. The first conductor 5 is helically coiled inside an insulating sleeve 10. The second conductor 6 is helically coiled around the insulating sleeve 10. The second conductor 6 is, in turn, enclosed in a second insulating sleeve 11. In order to achieve a flexible indifferent electrode 9 with a large electrode surface area, a part of the second sleeve 11 is made of a conductive polymer 12. The conductive polymer 12 directly abuts the second conductor 6 along the entire length of the section formed by the conductive polymer 12, so as to provide electrical contact between the conductive polymer and the second conductor 6.

Figure 3:
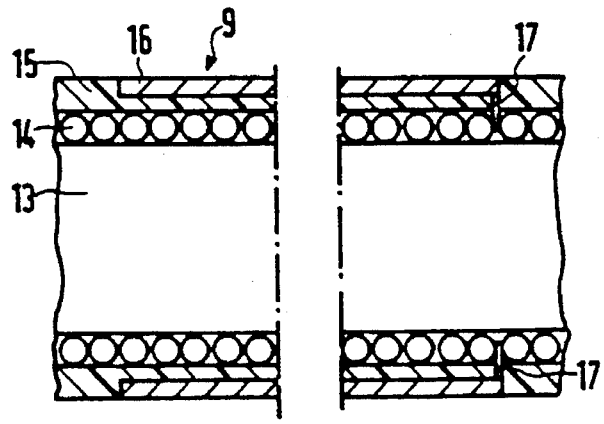
FIG. 3 is an enlarges sectional view of a second embodiment of an indifferent electrode in an electrode system constructed in accordance with the principles of the present invention.

A second embodiment for the indifferent electrode 9 is shown in FIG. 3. As in the embodiment of FIG. 2, a first conductor (not shown in FIG. 3) is enclosed in an insulating sleeve 13. A second helically coiled conductor 14 is coiled around the sleeve 13. A second insulating sleeve 15 encloses the second conductor 14. In this embodiment, the second insulating sleeve 15 is doped with a conductive, biocompatible material 16 along a defined section of the second insulating sleeve 15, so as to form the indifferent electrode 9. A separate conductor 17 electrically interconnects the doped coating 16 and the second conductor 14.

Appropriate materials for the doped coating 16 are, for example, biocompatible metals and metallic compounds, such as platinum and titanium nitride, or some other biocompatible conductive material, such as carbon. Because the conductive coating 16 consists of a doped section of the sleeve 15 and is not made of solid metal, it is sufficiently flexible for use, in principle, along the entire length of the electrode system 3.

The described exemplary embodiments may be combined in different ways. For example, the conductive polymer 12 in the embodiment of FIG. 2 may be replaced with a doped section along the entire sleeve 11, or the doped section 16 in FIG. 3 may be made of a conductive polymer. The conductive polymer may, in turn, be doped so as to further improve conductivity.

Although modifications and changes may be suggested by those skilled in the art, it is the intention of the inventors to embody within the patent warranted hereon all changes and modifications as reasonably and properly come within the scope of their contribution to the art.

We claim as our invention:

1. An implantable electrode system comprising:

an electrode lead having a proximal end adapted for connection to a medical apparatus for stimulating living tissue and a distal end adapted for introduction into a heart to be located adjacent living endocardial tissue to be stimulated;

said electrode lead having a flexible, insulating sleeve having a constant outer diameter between said proximal and distal ends, a first conductor extending through said sleeve between said proximal end and said distal end and being connectable at said proximal end to said medical apparatus, a tip electrode electrically connected to said first conductor and located at said distal end, and a second conductor, electrically insulated from said first conductor, contained in said insulating sleeve; and said insulating sleeve having a section made electrically conductive and forming an indifferent electrode, electrically connected to said second conductor, exposed at an exterior of said insulating sleeve, said section forming said indifferent electrode being substantially as flexible as a remainder of said insulating sleeve beyond said section and not enlarging said outer diameter, and said indifferent electrode having a length along said insulating sleeve so that a first portion of said indifferent electrode is disposed outside of said heart and a second portion of said indifferent electrode is disposed inside of said heart when said distal end is located adjacent said tissue to be stimulated in said heart.

2. An electrode system as claimed in claim 1 wherein said indifferent electrode comprises a conductive coating extending along a defined exterior section of said insulating sleeve, and wherein said second conductor and said conductive coating are electrically connected by a separate conductor extending through said insulating sleeve between said conductive coating and said second conductor.

3. An electrode system as claimed in claim 1 wherein said indifferent electrode comprises a conductive polymer.

4. An electrode system as claimed in claim 1 wherein said indifferent electrode comprises a section of said insulating sleeve doped with conductive material.

5. An electrode system as claimed in claim 4 wherein said section of said insulating sleeve is doped with a conductive material selected from the group consisting of biocompatible metals, metallic compounds and carbon.

6. An electrode system as claimed in claim 1 wherein said electrode lead further includes an additional insulating sleeve disposed inside said insulating sleeve, said second conductor being helically coiled in a space between said additional insulating sleeve and said insulating sleeve, and said first conductor being helically coiled inside said additional insulating sleeve.

* * * * *